US008569040B1

(12) United States Patent
Kroger et al.

(10) Patent No.: US 8,569,040 B1
(45) Date of Patent: Oct. 29, 2013

(54) NITRATE AND CARBONATE CONCENTRATION FOR HIGH GLUCOSE CONTENT IN MICROALGAE

(75) Inventors: Nils Kroger, Atlanta, GA (US); Stephen J. Miller, Richmond, CA (US); Nicole Poulsen, Atlanta, GA (US)

(73) Assignees: Georgia Tech Research Corporation, Atlanta, GA (US); Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 13/556,048

(22) Filed: Jul. 23, 2012

(51) Int. Cl.
*C12N 1/12* (2006.01)
*A01H 11/00* (2006.01)
*A01H 3/04* (2006.01)
*C12P 7/20* (2006.01)
*C12P 19/44* (2006.01)
*A01G 7/00* (2006.01)

(52) U.S. Cl.
USPC .......... 435/257.1; 435/41; 435/105; 435/946; 435/163; 435/74; 47/1.4

(58) Field of Classification Search
None
See application file for complete search history.

(56) References Cited

U.S. PATENT DOCUMENTS 4,320,594 A * 3/1982 Raymond .................. 47/1.4
2009/0004699 A1 * 1/2009 Tsuji et al. .................. 435/74

OTHER PUBLICATIONS

Yu, Eizadora T.; et al; "Triacylglycerol accumulation and profiling in the model diatoms *Thalassiosira pseudonana* and *Phaeodactylum tricornutum* during starvation" Journal of Applied Phycology, 21, 669-681, 2009.*
Enriched Seawate—Artificial Water Ingredient List, Baliga Lab, 2010.*
Gagneux-Moreaux, Sindy; et al; "Diatom artificial medium (DAM): a new artificial medium for the diatom *Haslea ostrearia* and other marine microalgae" Journal of Applied Phycology, 19, 549-556, 2007.*
Gardner, Robert D.; et al; "Use of sodium bicarbonate to stimulate triacylglycerol accumulation in the chlorophyte *Scenedesmus* sp and the diatom *Phaeodactylum tricornutum*" Journal of Applied Phycology, 24, 1311-1320, 2012.*
Yongmanitchai, W.; Ward, OP.; "Growth of and omega-3 fatty acid production by *Phaeodactylum tricornutum* under different culture conditions" Applied and Environmental Microbiology, 57, 419-425, 1991.*
Kester, Dana R. et al; "Preparation of Artificial Seawater" Limnology and Oceanography, 12, 176-179, 1967.*
Harrison, Paul J., et al. "A Broad Spectrum Artificial Seawater Medium for Coastal and Open Ocean Phytoplankton." Journal of Phycology 16:28-35 (1980). Print.

* cited by examiner

*Primary Examiner* — Blaine Lankford, Jr.
*Assistant Examiner* — David Berke-Schlessel

(57) ABSTRACT

The present invention pertains to compositions and methods for more efficiently and effectively growing microalgae suitable for biofuel production. In one aspect, the invention pertains to a composition comprising microalgae and a suitable growth medium. The suitable growth medium comprises a nutritionally acceptable nitrate salt, and a carbonate salt. The concentration of nutritionally acceptable nitrate salt is from about 75 to about 200 μM while the concentration of carbonate salt is from about 1 to about 6 mM.

20 Claims, 2 Drawing Sheets

NITRATE AND CARBONATE CONCENTRATION FOR HIGH GLUCOSE CONTENT IN MICROALGAE

FIELD

The invention relates generally to compositions and methods for more efficiently and effectively growing microalgae suitable for biofuel production.

BACKGROUND AND SUMMARY OF THE INVENTION

Microalgae typically grow in water when exposed to proper nutrients, light, and carbon dioxide. Microalgae growth has been an increasing focus recently as a useful way to create biomass which can then be employed to make biofuels. Microalgae may be preferable to terrestrial crops because microalgae often grow more quickly and do not interfere with food sources. Also, microalgae can often be grown using non-potable saline water and/or waste water. Advantageously, microalgae growth is also beneficial in fixing carbon dioxide which is a greenhouse gas.

Unfortunately, advances need to be made before bioethanol can efficiently and cost-effectively be produced from microalgae. For example, the yield of glucose from the microalgae needs to be increased. This, in turn, increases any alcohol yield from the fermentation of the glucose. Similarly, any increased glucose yield from the microalgae needs to be stable and/or predictable for a given type and/or amount of nutrient(s). Moreover, compositions of nutrients for achieving effective and efficient microalgae growth are needed.

Advantageously, the present invention addresses one or more of the aforementioned needs. In one embodiment the present invention pertains to a composition comprising microalgae and a suitable growth medium. The suitable growth medium typically comprises water, a nutritionally acceptable nitrate salt, and a carbonate salt. The concentration of nutritionally acceptable nitrate salt is usually from about 75 to about 200 µM and the concentration of carbonate salt is usually from about 1 to about 6 mM.

In another embodiment, the present invention pertains to a process for making a biofuel intermediumte. The process comprises supplying light to a suitable growth medium comprising microalgae and growing the microalgae in the suitable growth medium. The suitable growth medium often comprises water, a nutritionally acceptable nitrate salt, and a carbonate salt. The concentration of nutritionally acceptable nitrate salt is typically from about 75 to about 200 µM and the concentration of carbonate salt is typically from about 1 to about 6 µM. Next, the process comprises harvesting the microalgae. Advantageously, the harvested microalgae often comprise one or more of the following characteristics: (a) the microalgae yield at least about 5% w/w more glucose than microalgae grown in a comparable composition lacking the carbonate salt; (b) the microalgae stably yield at least about 15% w/w glucose; and (c) the microalgae yield at least about 5% w/w more glucose than microalgae grown in a comparable composition with 1500 µM of the same nitrate salt.

In yet another embodiment the invention pertains to a growth medium package for microalgae. The package usually comprises a nutritionally acceptable nitrate salt and a carbonate salt. The ratio of nitrate to carbonate is typically such that when the medium package is diluted to a suitable growth medium the concentration of nutritionally acceptable nitrate salt is from about 120 to about 170 µM and the concentration of carbonate salt is from about 2 to about 5 mM.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Figure 1:
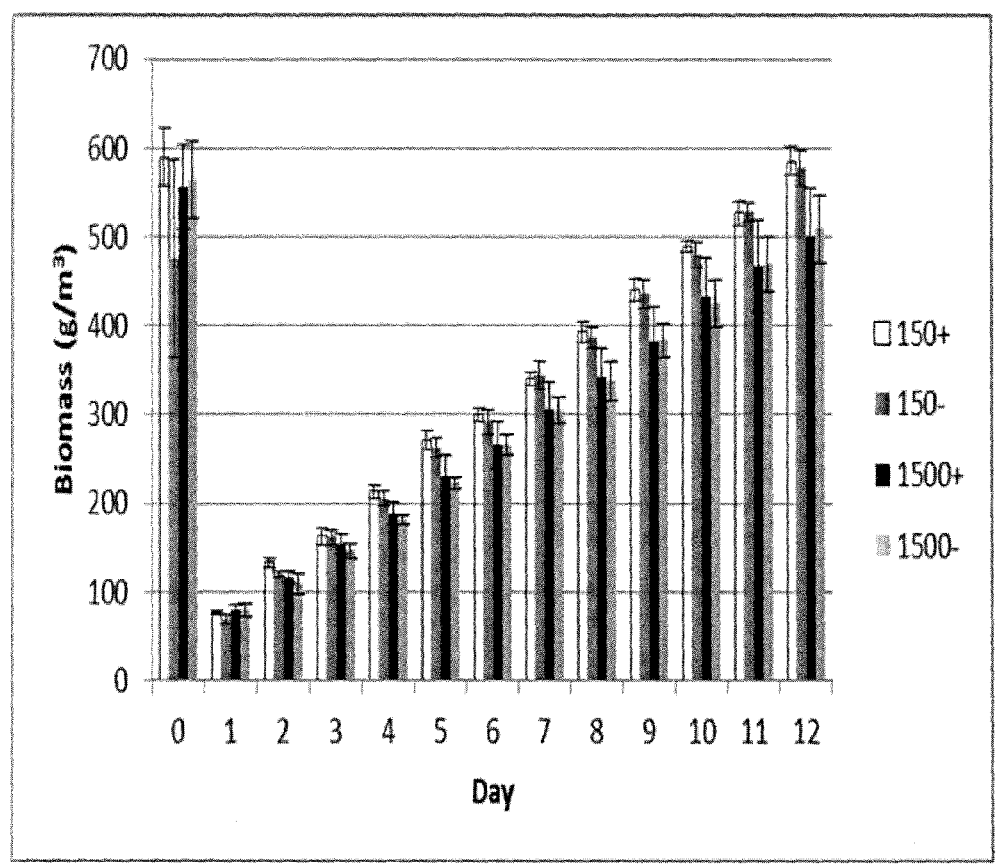
FIG. 1 depicts the biomass growth (g/m$^3$) of *Phaeodactylum tricornutum* over 12 days with an initial concentration of 150 µM or 1500 µM potassium nitrate (KNO$_3$) both with 3 mM sodium bicarbonate (NaHCO$_3$) as indicated by + and without sodium bicarbonate (NaHCO$_3$) as indicated by − in 10 liter cultures.

The present invention includes a number of embodiments. In one specific embodiment the invention pertains to a composition comprising microalgae and a suitable growth medium. The type of microalgae is not particularly critical and may be any beneficial microalgae. Microalgae that are particularly useful for biofuel applications include those that may produce relatively high amounts of glucose, require smaller amounts of nutrients and/or energy, and/or are able to be grown in relatively unpure water like seawater, brackish water, or waste water. Natural diatom microalgae like those from the genus *Phaeodactylum*, e.g., *Phaeodactylum tricornutum* may be particularly useful in the present invention. Of course, genetic or metabolically-altered miroalgae may be employed as well.

The amount and type of ingredients in a suitable growth medium may vary depending upon the particular type of microalgae being employed and the conditions to which it is being exposed such as type and amount of light. Generally, the suitable growth medium employed comprises water, a nutritionally acceptable nitrate salt, and a carbonate salt. The specific type, as well as, the relative amounts of nutritionally acceptable nitrate salt and carbonate salt may also vary depending upon the particular type of microalgae being employed, the conditions to which it is being exposed, and/or the desired results.

The specific nitrate salt employed is not particularly critical and is usually any which is nutritionally acceptable for the given type of algae. It is preferable that the nitrate salt or salts employed not be particularly toxic and therefore lighter metals are often preferable for the cation or cations in the nitrate salts. Generally, metals lighter than copper may be employed as a cation. Suitable cations include, for example, alkali metal, alkaline earth metal, aluminum, scandium, chromium, manganese, iron, cobalt, nickel, and mixtures thereof. Particularly preferable nitrate salts include potassium nitrate, sodium nitrate, and mixtures thereof.

As described above, the amount of nitrate salt varies depending upon a number of factors including the particular type of microalgae, type of nitrate salt, other ingredients and conditions employed and desired results. Generally, to facilitate and optimize biomass and/or glucose production, the initial concentration of nitrate salt is usually at least about 75, or least about 85, or at least about 120, or at least about 140 μM. On the other hand, the initial concentration of nitrate salt is not so high as to inhibit or substantially hinder biomass and/or glucose production. Generally, the initial concentration of nutritionally acceptable nitrate salt is less than about, or less than about 180, or less than about 170, or less than about 160 μM.

Generally, the type of carbonate salt employed is not particularly critical so long as the carbonate salt is substantially soluble in the aqueous medium to be employed. Particularly useful carbonate salts include those with a cation or cations selected from one or more alkali metal cations. A particularly preferable carbonate salt includes sodium bicarbonate.

The initial concentration of carbonate salt may vary depending upon, for example, the other ingredients and desired results. Useful initial concentrations of carbonate salts are usually at least about 1, or at least about 2, or at least about 3 mM. On the other hand, the initial concentration should not be so high as to inhibit or substantially hinder biomass and/or glucose production. In this regard, useful initial concentrations are typically less than about 6, or less than about 5, or even less than about 4 mM.

The aforementioned nitrate and carbonate salts may be conveniently packaged in a growth medium package for microalgae. When doing so it is often useful to select a ratio of nitrate to carbonate such that when the medium package is diluted with, for example, water to a suitable growth medium the concentration of nutritionally acceptable nitrate salt is from about 120 to about 170 μM and the concentration of carbonate salt is from about 2 to about 5 mM. In this manner the pre-packaged growth medium package may be simply added to an aqueous medium comprising microalgae such as, for example, *Phaeodactylum tricornutum*.

Advantageously, the aforementioned compositions may be usefully employed in processes for making a biofuel intermediumte. Such processes typically comprise first supplying light to a suitable growth medium comprising microalgae and then growing the microalgae in the suitable growth medium comprising water, nutritionally acceptable nitrate salt, and carbonate salt. The amount and type of water employed may vary depending upon the nutrients required and type of microalgae. Advantageously, in some instances municipal wastewater, seawater or water with high salinity can be used. That is, the water employed may have a concentration of sodium chloride of up to about 40 g/L (4%) which means that potentially seawater which usually has an approximate average sodium chloride concentration of about 35 g/L (3.5%) may be employed in some applications of the invention.

The microalgae may be grown in any convenient system. For example, the microalgae may be conveniently grown in suspension-based open ponds, enclosed photobioreactors, or combinations thereof. Open ponds are often simple, shallow ponds wherein microalgae may be cultured under conditions identical to their natural environment. The ponds may be designed in a raceway configuration wherein a paddlewheel or other device provides circulation and mixing of the microalgal cells and nutrients. Baffles may be used to guide the flow around bends and minimize space. The system may be operated continuously by adding the medium packages in advance of the paddle wheel. Microalgae may be harvested after circulation.

Alternatively or additionally, photobioreactors may be employed for microalgae growth. This is often beneficial when there are contamination and/or evaporation issues in an open pond. In addition, photobioreactors offer an advantage in that the conditions can usually be more effectively controlled than in an open pond. The photobioreactor is usually made of translucent materials for illumination by natural light although artificial light may also be employed. Often a pump or other mixing means is part of the system to maintain a turbulent flow and prevent settling. Advantageously, the photobioreactor may be integrated with a carbon dioxide source such as a power plant to efficiently use waste carbon dioxide generated.

The growth conditions in a pond, photobioreactor, or other system, of course, vary depending upon the type of microalgae and other ingredients. The culture temperature is generally between 15 and 30° C. (~60-80° F.) for optimal growth. In addition to the carbonate and nitrate salts and water described above, the growth medium may also comprise other inorganic nutritional elements such as, for example, nitrogen, phosphorus, iron, and/or silicon. Typically, nutrients are provided while microalgae are reproducing which is most of the time they are subjected to light.

After the microalgae have been grown they may be harvested for further processing. The manner of processing is not particularly critical and the selected manner may sometimes depend upon the type of products desired. Usual harvest methods include, for example, gravity settlement, centrifuge, and/or other physical separation methods. Typically, oil comprised in the biomass may be removed by convenient means such as solvent extraction and then can be further processed into, for example, biodiesel while the remainder of the biomass may be processed into, for example, bioethanol products. In addition to biofuels, the harvested microalgae may have other beneficial uses such as, for example, as fertilizer and/or pollution control through carbon dioxide use.

Advantageously, microalgae subjected to the aforementioned nitrate and carbonate initial concentrations have desirable characteristics. These characteristics include one, two or even all three of the following: (a) the microalgae yield at least about 5, or at least about 6, or at least about 7.5% w/w more glucose than a comparable nutrient medium composition lacking the carbonate salt; (b) the microalgae stably yield at least about 15, or at least about 18, or even at least about 20% w/w glucose; and (c) the microalgae yield at least about 5% w/w more glucose than microalgae grown in a comparable composition with 1500 μM of the same nitrate salt. Advantageously, these potential yields mean that growing microalgae may provide an effective and efficient way of making useful products such as bioethanol.

The aforementioned characteristics may be determined with respect to a nutrient medium composition or growth medium such as the one described in Example 1 below.

EXAMPLES

The present invention is further illustrated by the following examples which should not be construed as limiting. The contents of all references, patents and published patent applications cited throughout this application, as well as the Figures and Tables are incorporated herein by reference.

Example 1

300 mL Cultures

The amount of both nitrogen and carbonate can influence the intracellular accumulation of chrysolaminaran (CHL) which is a glucose polymer from which monomeric glucose can be generated by acid hydrolysis with often a near 100% yield. The growth rates of *P. tricornutum* (determined as number of cells per ml, and as dry weight in g of biomass per m³) and CHL production (determined as glucose level in hot water extract after acid hydrolysis) were monitored over multiple growth and dilution cycles to establish reproducible growth conditions and to observe the effects of nitrate and carbonate concentration.

Two nitrate concentrations were chosen for the large scale cultivation, "high N" (1500 μM KNO$_3$) and "low N" (150 μM KNO$_3$), with and without the addition of 3 mM NaHCO$_3$. The rest of the growth medium employed in example 1 was as follows:

Medium Composition

| Component | Concentration |
|---|---|
| Glycylglycine | 4 mM |
| NaCl | 0.4 M |
| CaCl2 | 7.5 mM |
| MgCl$_2$•6H$_2$O | 20 mM |
| MgSO$_4$•7H$_2$O | 20 mM |
| KCl | 4 mM |
| KNO$_3$ | 1.5 mM |
| Thiamine | 1.6 μM |
| K$_2$HPO$_4$ | 200 μM |
| Na$_2$EDTA•2H$_2$O | 16 μM |
| H$_3$BO$_3$ | 18 μM |
| ZnCl$_2$ | 4.5 μM |
| CuCl$_2$•H$_2$O | 1.6 μM |
| Na$_2$MoO$_4$•2H$_2$O | 1 μM |
| CoCl$_2$•6H$_2$O | 1.8 μM |
| FeCl$_2$•4H$_2$O | 4.9 μM |
| MnCl$_2$•4H$_2$O | 1.8 μM |
| NaHCO$_3$ | 3 mM |

Figure 2:
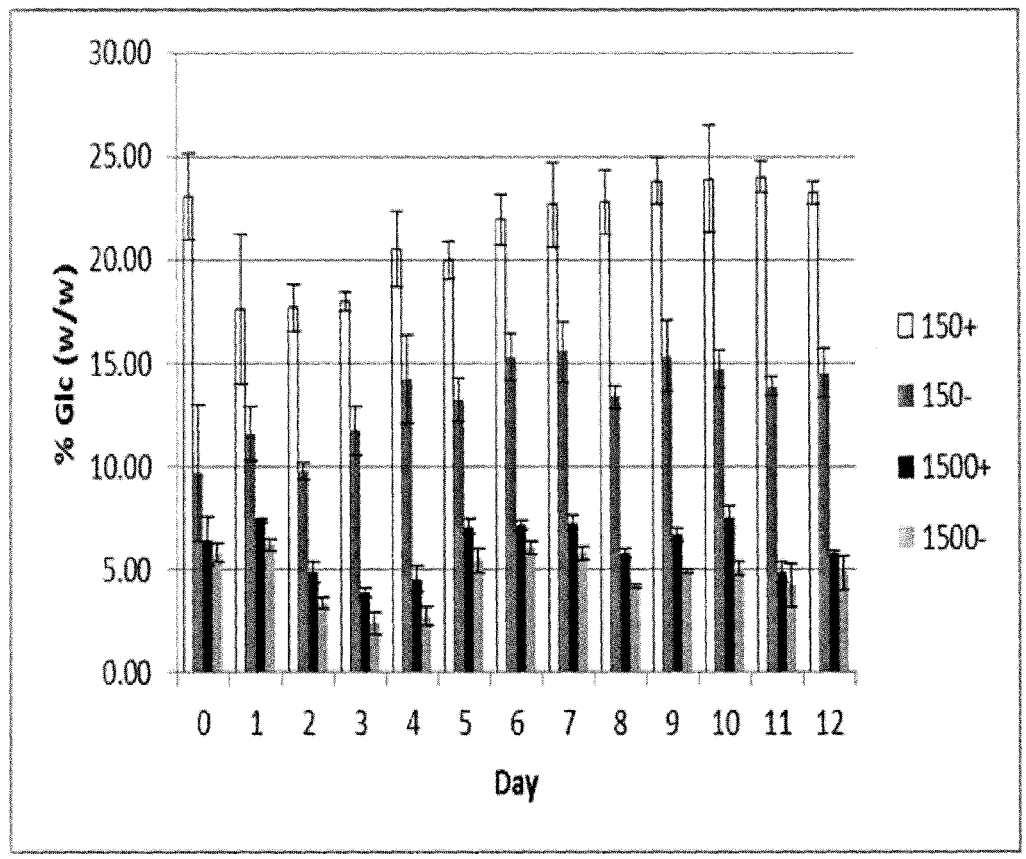
FIG. 2 depicts the glucose content (w/w %) of *Phaeodactylum tricornutum* over 12 days with an initial concentration of 150 µM or 1500 µM potassium nitrate (KNO$_3$) both with 3 mM sodium bicarbonate (NaHCO$_3$) as indicated by + and without sodium bicarbonate (NaHCO$_3$) as indicated by − in 10 liter cultures.

Cells grown in both the presence and absence of 3 mM NaHCO$_3$ displayed similar growth rates with respect to both cell number and biomass production (FIGS. 1 and 2). Following dilution into fresh medium, cells grown in "low N" in the presence of carbonate typically had a decrease in CHL content from ~25% w/w to ~15-17.5% w/w. This was then advantageously followed by a relatively fast recovery in 4 days to the pre-dilution value of >20% w/w. (FIGS. 1 and 2, Table 1). Cells grown in the "high N" reached a CHL content less than about 10%. Each data point of FIGS. 1-2 represents the average of three experiments while the error bars indicate standard deviation.

Culture Conditions

*Phaeaodactylum tricornutum* was grown at 18° C. with a 14 h light/10 h dark cycle in artificial sweater medium (minus silicate) containing KNO$_3$ as the sole nitrogen source. The concentration of KNO$_3$ in the medium varied between 10-1500 μM. Where indicated 3 mM NaHCO$_3$ was also added to the ASW medium. Cell counts were measured using the TC10 cell counter (Biorad). Prior to cell counting the culture was diluted appropriately to contain between $1 \times 10^5$-$1 \times 10^7$ cells/ml and then vortexed for 60 seconds to break up clumps.

Determination of Intracellular Chrysolaminaran (Glc) Content

Cells were harvesting by centrifugation (10 min, 3000×g) and lyophilized. Cell biomass was determined gravimetrically and 50 μl water was added per mg of dry cell pellet and then vortexed to homogeneity. The cells were extracted at 110° C. for 1 h, followed by centrifugation for 5 min at 16,000×g and the supernatant ("hot water extract") was transferred to a fresh tube. The hot water extract was hydrolyzed with 5% H$_2$SO$_4$ at 110° C. for 2 h, neutralized with NaOH, diluted with H$_2$O, and then the Glc content was determined using high pressure anion exchange chromatography combined with amperometric detection (HPAEC-PAD) on a Carbopac PA20 column (Dionex). The running conditions were as follows: an isocratic gradient of 10 mM NaOH for 17 minutes at 0.4 ml/min followed by an isocratic gradient of 200 mM NaOH for 10 min and then an equilibration of 30 minutes in 10 mM NaOH prior to the start of the next sample.

Table 1 is a comparison of maximum and minimum Glc content (% w/w) and productivity over a 12 day growth period of *Phaeodactylum tricornutum* with initial concentrations of 150 and 1500 μM nitrate both with 3 mM sodium bicarbonate (NaHCO$_3$) as indicated by + and without sodium bicarbonate (NaHCO$_3$) as indicated by – in 10 liter cultures in the growth medium described above.

TABLE 1

|  | 150 μM nitrate | | 1500 μM nitrate | |
|---|---|---|---|---|
| carbonate | + | – | + | – |
| Max. Content % Glc (w/w) | 24.0 ± 0.8 | 15.56 ± 1.5 | 7.54 ± 0.6 | 6.2 ± 0.3 |
| Min. Content % Glc (w/w) | 17.62 ± 3.6 | 9.7 ± 3.3 | 3.89 ± 0.2 | 2.38 ± 0.5 |
| Max. mg Glc/L | 134.5 (Day 12) | 83.8 (Day 12) | 28.9 (Day 12) | 24.6 (Day 12) |
| Min. mg Glc/L | 13.5 (Day 1) | 7.9 (Day 1) | 5.8 (Day 1) | 4.9 (Day 1) |

FIG. 1 shows the biomass (g/m³) of *P. tricornutum* grown over a 12 day period with initial concentrations of 150 and 1500 μM nitrate both with 3 mM sodium bicarbonate (NaHCO$_3$) as indicated by + and without sodium bicarbonate (NaHCO$_3$) as indicated by – in 10 liter cultures. Neither the concentration of nitrate nor the addition of carbonate significantly effects the biomass production of *P. tricornutum*.

FIG. 2 shows the Glucose content (% w/w) of *P. tricornutum* grown over a 12 day period with initial concentrations of 150 and 1500 μM nitrate both with 3 mM sodium bicarbonate (NaHCO$_3$) as indicated by + and without sodium bicarbonate (NaHCO$_3$) as indicated by – in 10 liter cultures.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A composition comprising microalgae and a suitable growth medium wherein the suitable growth medium comprises water, a nutritionally acceptable nitrate salt, and a carbonate salt;
   wherein the concentration of nutritionally acceptable nitrate salt is from 75 to 200 μM and the concentration of carbonate salt is from 1 to 6 mM.

2. The composition of claim 1 wherein the microalgae comprises diatom microalgae.

3. The composition of claim 1 wherein the microalgae comprises *Phaeodactylum tricornutum*.

4. The composition of claim 1 wherein the nitrate salt is selected from the group consisting of an alkali metal nitrate, an alkaline earth metal nitrate, aluminum nitrate, scandium nitrate, chromium nitrate, manganese nitrate, iron nitrate, cobalt nitrate, nickel nitrate, and mixtures thereof.

5. The composition of claim 4 wherein the nutritionally acceptable nitrate salt is potassium nitrate.

6. The composition of claim 1 wherein the carbonate salt is water-soluble.

7. The composition of claim 1 wherein the carbonate salt is an alkali metal carbonate.

8. The composition of claim 1 wherein the carbonate salt is sodium bicarbonate.

9. The composition of claim 1 wherein the concentration of nutritionally acceptable nitrate salt is from about 120 to about 170 µM.

10. The composition of claim 1 wherein the concentration of carbonate salt is from about 2 to about 5 mM.

11. The composition of claim 1 wherein the microalgae grown in said growth medium yields at least about 5% w/w more glucose than microalgae grown in a comparable composition lacking the carbonate salt.

12. The composition of claim 1 wherein the microalgae grown in said growth medium yields at least about 7.5% w/w more glucose than microalgae grown in a comparable composition lacking the carbonate salt.

13. The composition of claim 1 wherein the microalgae grown in said growth medium stably yields at least about 15% w/w glucose.

14. The composition of claim 1 wherein the microalgae grown in said growth medium stably yields at least about 18% w/w glucose.

15. The composition of claim 1 wherein the microalgae grown in said growth medium yields at least about 10% w/w more glucose than microalgae grown in a comparable composition with 1500 µM of the same nitrate salt.

16. A process for making a biofuel intermediate comprising:
(1) supplying light to a suitable growth medium comprising microalgae; and
(2) growing the microalgae in the suitable growth medium; wherein the suitable growth medium comprises water, a nutritionally acceptable nitrate salt, and a carbonate salt and wherein the concentration of nutritionally acceptable nitrate salt is from 75 to 200 µM and the concentration of carbonate salt is from 1 to 6 µM; and
(3) harvesting the microalgae wherein the harvested microalgae comprise one or more of the following characteristics: (a) the microalgae yield at least 5% w/w more glucose than microalgae grown in a comparable composition lacking the carbonate salt; (b) the microalgae stably yield at least 15% w/w glucose; and (c) the microalgae yield at least 10% w/w more glucose than microalgae grown in a comparable composition with 1500 µM of the same nitrate salt.

17. The process of claim 16 wherein the harvested microalgae comprise two or more of the following characteristics: (a) the microalgae yield at least about 5% w/w more glucose than microalgae grown in a comparable composition lacking the carbonate salt; (b) the microalgae stably yield at least about 15 w/w glucose; and (c) the microalgae yield at least about 10% w/w more glucose than microalgae grown in a comparable composition with 1500 µM of the same nitrate salt.

18. The process of claim 16 wherein the harvested microalgae comprise the following characteristics: (a) the microalgae yield at least about 5% w/w more glucose than microalgae grown in a comparable composition lacking the carbonate salt; (b) the microalgae stably yield at least about 15% w/w glucose; and (c) the microalgae yield at least about 10% w/w more glucose than microalgae grown in a comparable composition with 1500 µM of the same nitrate salt.

19. A growth medium package for microalgae comprising a nutritionally acceptable nitrate salt and a carbonate salt; wherein the ratio of nitrate to carbonate is such that when the medium package is diluted to form a suitable growth medium the concentration of nutritionally acceptable nitrate salt is from 120 to 170 µM and the concentration of carbonate salt is from 2 to 5 mM.

20. The growth medium package of claim 19 wherein *Phaeodactylum tricornutum* microalgae grown on the medium diluted to form a suitable growth medium stably yield at least about 18% w/w glucose.

\* \* \* \* \*